United States Patent
Lechner et al.

(10) Patent No.: US 9,401,983 B2
(45) Date of Patent: Jul. 26, 2016

(54) CHEMICAL ALERT SYSTEM USING A PROTABLE DEVICE WITH INTEGRATED CHEMICAL SENSOR

(71) Applicant: Sensirion AG, Stafa (CH)

(72) Inventors: Moritz Lechner, Uerikon (CH); Rafael Santschi, Zurich (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 14/161,137

(22) Filed: Jan. 22, 2014

(65) Prior Publication Data

US 2014/0225738 A1    Aug. 14, 2014

(30) Foreign Application Priority Data

Jan. 31, 2013 (EP) .................................... 13405028

(51) Int. Cl.
| | | |
|---|---|---|
| G08B 21/00 | (2006.01) | |
| H04M 1/725 | (2006.01) | |
| G08B 21/12 | (2006.01) | |
| G01N 27/12 | (2006.01) | |
| G08B 17/117 | (2006.01) | |

(52) U.S. Cl.
CPC ........... *H04M 1/72536* (2013.01); *G08B 21/12* (2013.01); *G01N 27/122* (2013.01); *G08B 17/117* (2013.01); *H04M 2250/12* (2013.01)

(58) Field of Classification Search
CPC .............................. G08B 21/182; G08B 21/12
USPC ............... 340/603, 539.11, 539.26, 628, 632;
436/147, 149, 120, 128, 132; 702/122,
702/30, 23; 422/83, 84
See application file for complete search history.

(56) References Cited

U.S. PATENT DOCUMENTS

| | | | | |
|---|---|---|---|---|
| 6,768,116 | B1 * | 7/2004 | Berman | ................... G01T 1/178 250/374 |
| 6,992,580 | B2 * | 1/2006 | Kotzin et al. | ............ 340/539.11 |
| 8,610,567 | B2 * | 12/2013 | Hamed et al. | ................. 340/540 |
| 2007/0005267 | A1 | 1/2007 | Li | |
| 2014/0084390 | A1 * | 3/2014 | Mayer et al. | ................... 257/414 |

OTHER PUBLICATIONS

Maged N. Boulos et al., "Crowdsourcing, Citizen Sensing and Sensor Web Technologies for Public and Environmental Health Surveillance and Crisis Management: Trends, OGC Standards and Application Examples", International Journal of Health Geographics 2011, vol. 10:67, pp. 1-29.

Jayanta Chakraborty, Mohuya Chakraborty, "Mobile Telephony Based Secured Society an Anti-Terrorism Attempt", Proc 2008 IEEC Tencon Conf. 19, Nov. 2008.

(Continued)

*Primary Examiner* — Toan N Pham
(74) *Attorney, Agent, or Firm* — Cooper & Dunham LLP

(57) ABSTRACT

A chemical alert system for generating an alarm is described including a portable electronic device, preferably with telecommunication capabilities to allow for data and/or voice communication via private or public networks, and at least one chemical sensor integrated with the housing of the portable device and controlled by a chemical sensor processing unit, further comprising an alert discriminator receiving input based on measurements of the chemical sensor, performing a test on the input and based on an outcome of the test initiating the transfer of measurements of the chemical sensor to a remote processing facility.

10 Claims, 4 Drawing Sheets

(56) References Cited

OTHER PUBLICATIONS

RJ Honicky et al., "N-Smarts: Networked Suite of Mobile Atmospheric Real-Time Sensors", NSDR, Seattle, Washington, USA, Aug. 18, 2012.

Michael Karst, "Humidity and Temperature Sensors in Mobile Phones", Sensirion AG, Switzerland, Apr. 18, 2012.

Anand D. Mane et al., "Explosive Detection with Mobile With Mobile Telephony an Attempt Towards a Safe Ambience", International Conference on Signal Processing, Communication, Computing and Networking Technologies, 2011, pp. 187-191.

* cited by examiner

CHEMICAL ALERT SYSTEM USING A PROTABLE DEVICE WITH INTEGRATED CHEMICAL SENSOR

FIELD OF THE INVENTION

The present invention relates to system for generating an alert or action in response to a change in the chemical composition of the surroundings of a portable electronic device such as a mobile phone, tablet and the like using a chemical sensor integrated within the housing of the device.

BACKGROUND OF THE INVENTION

Portable or mobile devices originally introduced as mobile phones or electronic agendas become more and more ubiquitous. As the processing power of their internal processors grows and equally the bandwidth for communication with stationary processors, such portable devices take on more and more the role of multi-purpose tools available to consumers and specialist users alike.

It has been recognized that portable devices can benefit from the presence of sensors capable of providing chemical analysis of materials brought into contact or the vicinity of the device. Whilst there are many possible applications for such sensors, it suffices to consider for example the analysis of air surrounding the portable device. Such an analysis can be useful for multiple purposes such as testing for hazardous gases, breath analysis for general medical purposes or driving fitness, and the like.

It has been known to incorporate gas sensors into portable sensor devices, such as mobile phones or tablet computers. For example, humidity sensors have been incorporated into some smartphone devices. However, humidity (i.e. gaseous water in air) is only one gas that might be of interest to a user of this type of device. Therefore, there is a need to provide devices that allow for measuring of a larger selection of gases, such as alcohol, CO, benzene, or groups of gases, which can e.g. be classified as certain smells or odors.

In case such gases can cause a hazard or pose an otherwise relevant condition for the user, it is desirable to use portable devices with integrated chemical sensors to issue an alarm or a notification to its user, to the surrounding of the user or to a remote location or to trigger an automated response.

As the issuing of a false hazard alarm or the triggering of an automated response can be disruptive and costly, it is seen as an object of the invention to improve the reliability of an alert system based on the use of portable devices with an integrated chemical sensor.

SUMMARY OF THE INVENTION

Hence, according to a first aspect of the invention, there is provided a chemical alert system for generating an alarm, the system including a portable electronic device, preferably with telecommunication capabilities to allow for data and/or voice communication via private or public networks, enclosed in a housing having preferably an air duct with an opening to the exterior of the housing and at least one chemical sensor controlled by a chemical sensor processing unit, further comprising an alert discriminator receiving input based on the measurements of the chemical sensor, performing a first test on the input and based on an outcome of the test initiating the transfer of measurements of the chemical sensor to a remote processing facility in case that, for example, the input from the chemical sensor unit indicates the presence of a chemical component in the sampled air beyond a test limit.

The test limit or threshold can be for example a concentration value or a condition or test procedure for the measurement results or any results derived from the measurements.

In a preferred embodiment the alert discriminator includes a two-stage test with a first threshold activating an alert mode in the portable device and a second threshold initiating either the transfer of measurements or the activation of an alarm mode of the portable device. In a variant of this embodiment, the passing of second threshold causes the activation of the alarm state, whereas the passing of the first threshold without passing of the second threshold initiates the transfer of measurements.

In a preferred embodiment of the invention the transfer of measurements includes measurements as used as input to the alert discriminator and additional measurements as gained from any prior stage in the processing of the measurements including raw data representing the direct sensor measurements.

An alarm of the portable device can include the generation of an acoustic alarm using internal resources such as a loudspeaker as integrated, or of an optical alarm using display or any in-built flash. Another possible alarm can be the initiation of a communication to a remote location, such as police or fire departments. An alarm can include a control event, in which the portable device controls one or more devices in its vicinity. It is further possible that the remote facility triggers the alarm by either assuming control of the portable device, other devices in its vicinity or by initiating communications to the remote locations.

Another aspect of the invention relates to a chemical alert system including a portable device as described above and a remote processing facility to receive the measurements of the chemical sensor as transferred by the portable device, whereby the remote facility is adapted to augment processing steps for the measurement of the chemical sensor as performed by the portable device.

The augmentation of the processing steps can include the re-processing of the measurements using more complex and powerful routines or models beyond the capacity of the portable device. The augmented processing can include the addition of further measurements or information from sources other than the portable device itself. Such sources can include other portable device in the vicinity of the portable device or the output of external sensors such as smoke or gas detectors. The further information may include publicly available information such as weather or other environmental conditions as may be useable for the interpretation of the measurement as performed by the portable device.

A preferred chemical sensor includes a sensor material, preferably in form of a layer, also denoted as receptor layer, to which an analyte may bond to and as such modify an electrical property of the sensor material such as its electrical conductance, e.g. metal oxide chemical sensors. It can also include a plurality of different sensors or an array of similar sensors. In such a sensor array, each sensor cell may provide a layer of a material exhibiting different absorption characteristics such that each cell of the sensor array may specifically be sensitive to a different analyte and as such may enable the portable electronic device to detect the presence or absence or concentration of such analyte.

A preferred sensor is combined with a least part of its control and read-out circuit onto a single semiconductor substrate. In a preferred variant this circuit is a CMOS circuit.

The portable device can be a smart phone, a handheld computer, a laptop, an electronic reader, a tablet computer, a game controller, a pointing device, a photo or a video camera, a digital music player, an electronic wrist watch, a personal health tracking device, a headset or a computer peripheral. Its housing is typically a shell of metal, glass, or plastic material and can be assembled as a unibody or from several parts. Enclosed in the housing are typically processors, drivers for parts such as screens, antennae, cameras, microphones and speakers as well as batteries to provide power to the device and its parts. A screen is typically arranged as a part of the housing or mounted behind a transparent window of the housing.

The duct acts as confinement for the air inside the housing and can take the shape of a tube or channel formed as part of the housing or as a separate part connected to an opening in the housing. It can be a single straight or curved duct.

The opening itself can be a dedicated opening thus exclusively connecting the chemical sensor to the outside. However, given that the manufacturers of portable electronic devices strive to maintain the housing as a good protection against humidity and water, it is seen as advantageous that the opening is shared with at least one further component of the portable device requiring a similar connection to the exterior, such as other sensors, for example humidity sensors, a loudspeaker, or a microphone. The opening can further be protected by a grill or a membrane to prevent bigger particles or unwanted components of the air from entering or blocking the duct.

The above and other aspects of the present invention together with further advantageous embodiments and applications of the invention are described in further details in the following description and figures.

DETAILED DESCRIPTION

Figure 1A:
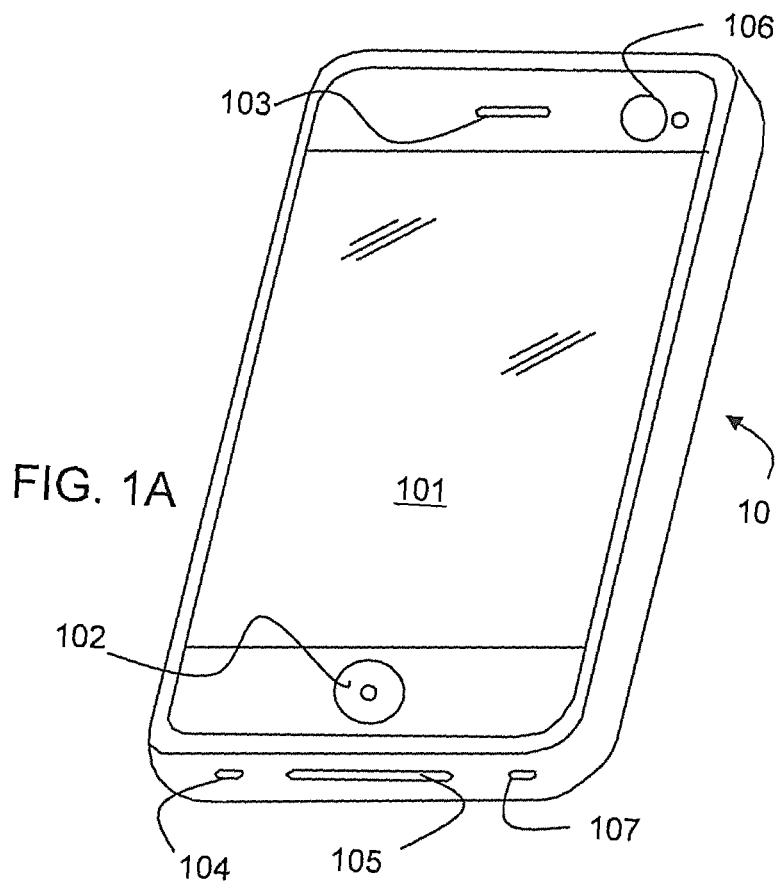
FIG. 1A is a perspective view of a portable electronic device.

The device of FIG. 1A is a portable electronic device such as a mobile phone. The housing 10 of the mobile phone includes a front side with a screen 101 and elements like buttons 102 to let a user interact with the phone. Also shown on the front side is an opening 103 for a loudspeaker. Further openings 104, 105 are located at a lower side wall of the housing 10. It is well known to mount components like microphones and loudspeakers behind such openings. The phone includes one or two cameras 106, and internally additional sensors (not shown) such as location sensors or GPS, and acceleration and orientation sensors in a manner well known.

Figure 1B:
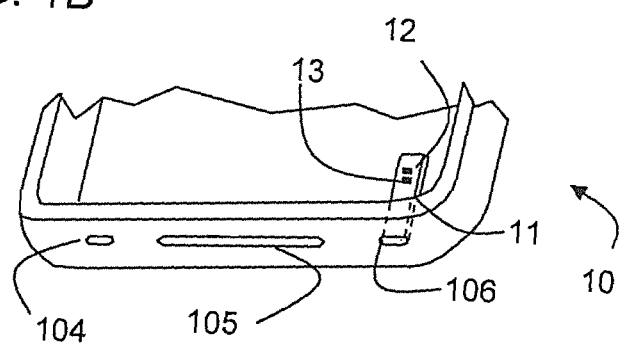
FIG. 1B is a schematic view into part of the housing of the device of FIG. 1A.

Another opening 107 is located at the lower side wall. As shown in FIG. 1B the opening 107 is linked to a tubular duct 11 passing through the interior of the housing. A chemical sensor 12 and a humidity sensor 13 are both mounted along the duct 11 such that the sensitive areas of both sensors are essentially exposed air of the same composition entering the duct through the opening 107. The actual size and shape of the duct 11 depends on the volume available and the nature of the chemical gas sensor 12 and the humidity sensor 13 can vary, but given the physical constraints of portable mobile devices the area of the opening is typically in the range of less than 10 square millimeters and in the present example actually about less than 3.1 square millimeters.

Figure 2:
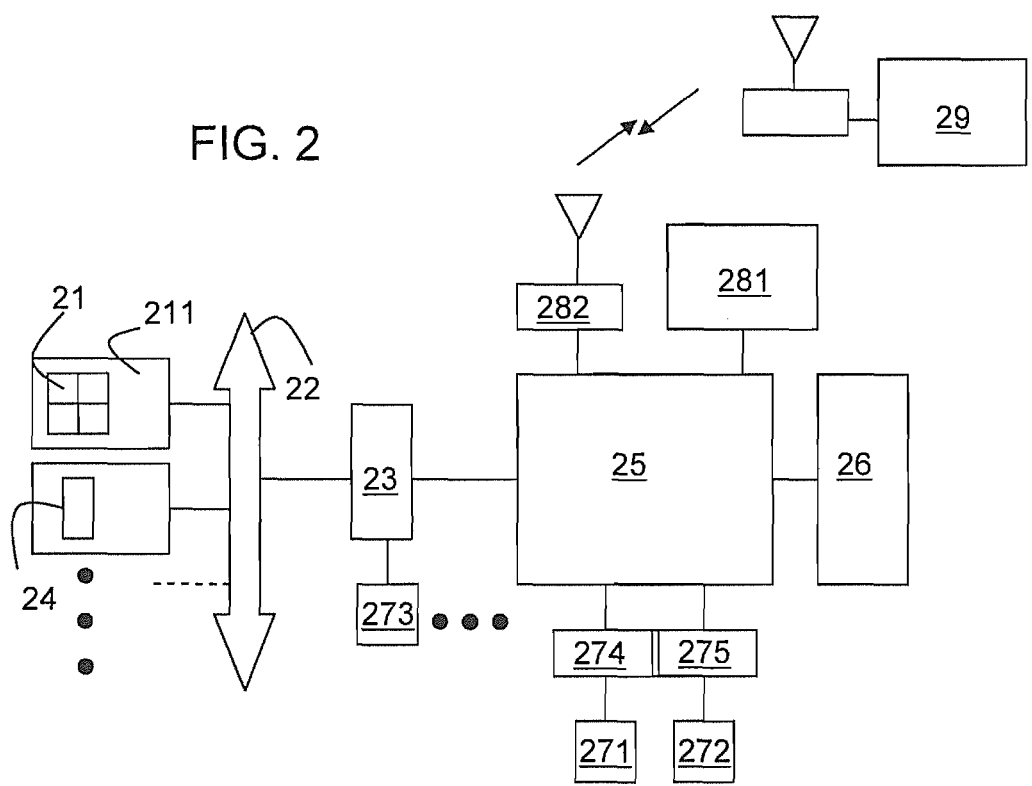
FIG. 2 is a block diagram with components of a portable device in accordance with an example of the invention.

FIG. 2 shows a block diagram with the most important components of the portable device. In particular, the device includes a chemical gas sensor 21 integrated as part of a CMOS substrate 211 which has CMOS circuitry to control the basic functions and the basic readout of the sensor. The CMOS circuit can include for example the driver to switch the sensor and his heater on or off as well as A/D converters and amplifiers and an I2C bus controller to exchange data on an I2C bus 22. The I2C bus connects the sensors with a sensor hub 23. A further humidity and temperature sensor 24 is also linked to the I2C bus 22. The chemical sensor 21 can be for example a single sensor, such as a metal oxide type sensor, or an array or assembly of several sensors. The chemical sensors can be either of the same type of metal oxide sensors but with a different sensing material or, either alternatively or in addition, sensors based on a different sensing principle. For metal oxide sensors, SnO2 (tin dioxide) is known to be sensitive to carbon monoxide, and WO3 (tungsten trioxide) is known to be sensitive to O3 (Ozone).

The sensor hub 23 provides a control and processing unit for more complex control and read-out functions of the chemical sensor 21 based on signals sent to or extracted from, respectively, the on-chip CMOS circuitry. The sensor hub 23 also controls other auxiliary sensors such as GPS, magnetometers, accelerometers and the like.

Further control and read-out function can also be performed by the central processing unit (CPU) 25 of the portable device, which in turn has read/write access to a memory 26, which can include static or volatile memory or both as known in the art. The memory 26 typically stores the operating system of the device and can also be used to store application programs specific to the operation of the sensors of the portable device. The functions performed by the sensor hub and the sensor specific programs and program libraries as stored and executed by the CPU 25 form a chemical processing unit capable of transforming the measurements of the sensor into a result which can be displayed or otherwise communicated to the user of the portable device.

The CPU 25 and the memory 26 include and execute an alert discriminator in form of executable code. Functions of the alert discriminator are described in more detail below while making reference to FIG. 3.

In addition to the specific sensors as described above, the CPU is also connected to one or more sensors, for example the camera 271 or the microphone 272 also shown as the camera 106 and the microphone 104 of FIG. 1. Other sensors 273 such as location, acceleration and orientation sensors can be controlled by the sensor hub 23 as shown in the example. The sensors 271, 272 communicate with the CPU using their own interface units 274, 275, respectively, which operate typically in complete independence of the chemical sensor 21.

The device includes further well known input/output units 281 such as a touch sensitive display, virtual or physical keyboards and gesture tracking devices etc. The portable device as shown has a telecommunication circuit 282 comprising an antenna, driver circuits and encoding and decoding units as are well known in the art. Using such a telecommunication circuit, the device can connect to remote data processing and storage facilities 29 as shown.

Figure 3A:
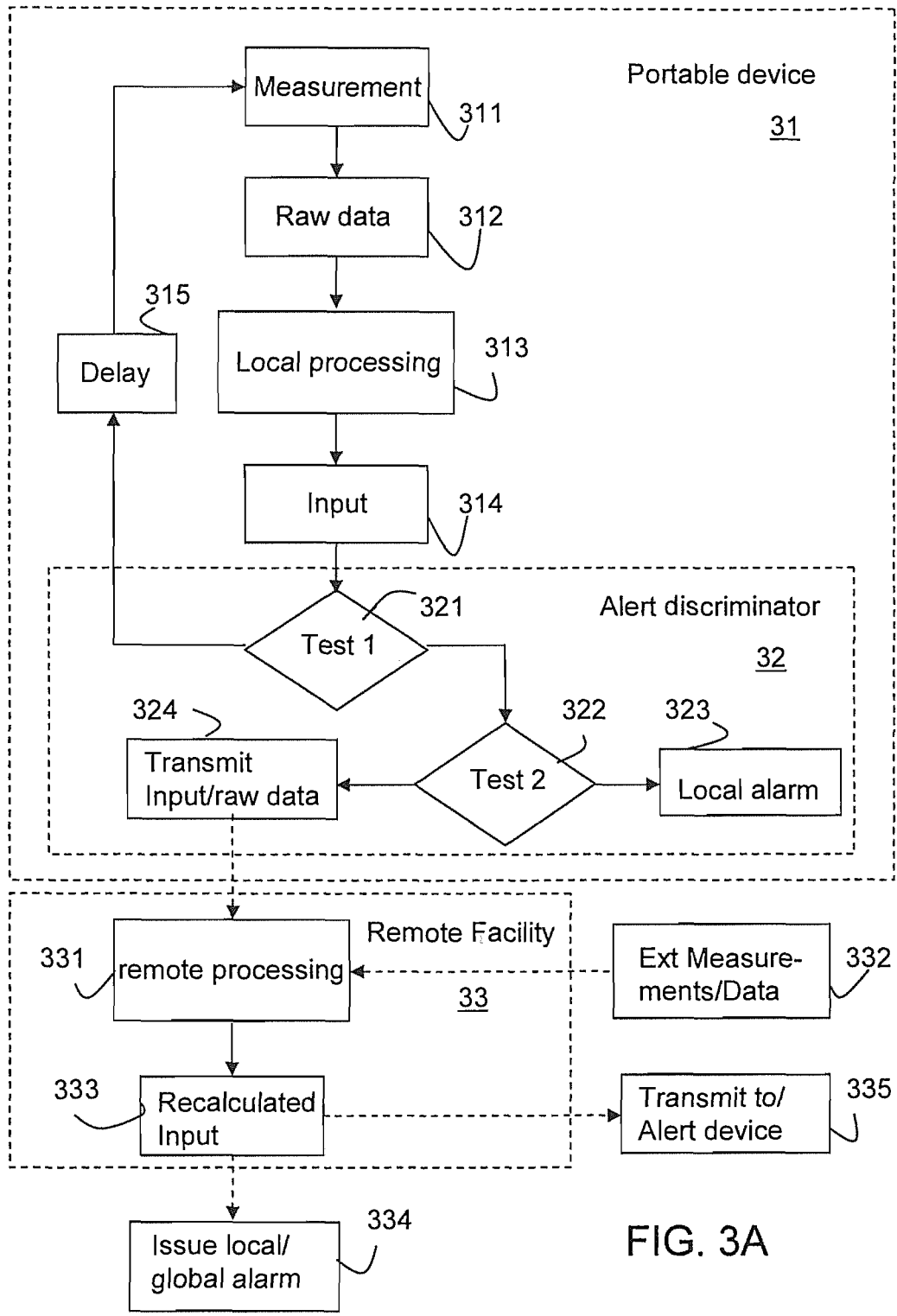
FIG. 3A illustrates processing steps in accordance with an example of the invention.
Figure 3B:
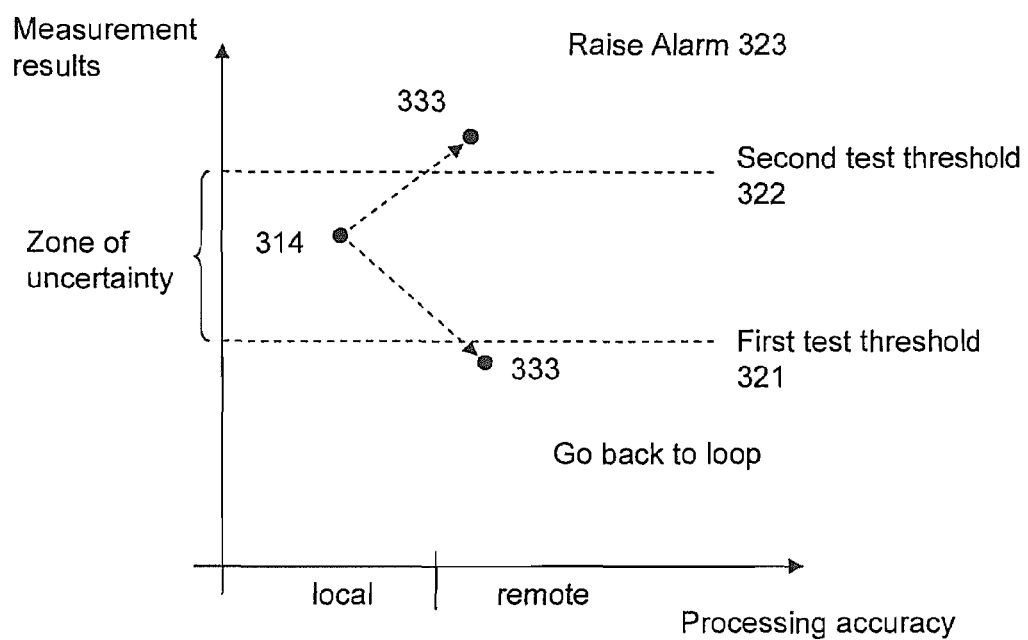
FIG. 3B illustrates the effects of a recalculated chemical measurement in an example of the invention.

The FIG. 3 illustrate the operation of the above described elements in form of the schematic flow diagram of FIG. 3A and the basic diagram of FIG. 3B, which illustrates the effect of the recalculation of a measurement or input as described below.

A first part 31 of the processes described are performed within and by the portable device. These local processes 31 performed by the portable device include the processes 32 performed by the alert discriminator. Other remote processes 33 involve and are performed within the remote facility.

The processes can be started for example by a user selecting an alert function or program on the portable device. Once started, the program keeps the portable device in a measurement loop. In the measurement loop measurements 311 are taken. The raw data from the measurement are then processed in a local processing step 312 performed by the chemical processing unit of the portable device.

The processing step 312 can include the application of standard routines and basic functions such as baseline corrections, polynomial fits, max-min determination, derivative or integral calculations, spectral analysis such as FFT or DFT, filtering, matrix calculations etc. The routines can further include more complex variants of statistical analysis tools such as Principal Component Analysis, Linear Discriminant Analysis and the like or neural network based tools such as Self-organizing Maps, Back Propagation, pattern recognition routines etc.

As the exact nature of the routines is not seen as a specific aspect of the present example, it suffices to refer to known libraries of such routines as available for example in MAT-LAB®.

The processed data are used as an input 313 to the alert discriminator 32. Within the alert discriminator the input is used in a first test 321. The first test compares the input 313 or values derived from the input 313 against a first condition or threshold. The threshold can be for example a concentration value for a specific gas or component or a plurality of concentrations for a spectrum of gases.

The portable device remains in its measurement loop, in case the first test 321 is negative, and after a delay 315 the sensor is automatically activated to perform another measurement 311. The delay is chosen to repeat measurements as often as possible without however draining the battery of the portable device. Hence the delay 315 is automatically switchable depending on whether the portable device is charging and thus connected to an external power supply or not.

If the outcome of the first test 321 is however positive, the input 313 or values derived from the input 313 are subject to a second test 322. Typically the second test 322 would set stricter conditions or thresholds. If the outcome of the second test 322 is positive, a local alarm 323 is raised instantly by either activating suitable resources within the portable device itself or by sending out communications using the communication facilities build into the portable device. The local resources can include the loudspeaker for generating an acoustic alarm, or the display or flash for generating an optical alarm or both. Depending on the type of portable device, the communication can be transmitted over a local or wide area network, or over the public telecommunication network. The communication can be an alert message to emergency services, to carers and/or to other authorities or people concerned with the well-being of the user.

The local alarm 323 can also be integrated into a home automation system and thus initiate an automated response to the alarm such as starting fire sprinklers, shutting down appliances, triggering a house alarm and the like.

If however the second test 322 is negative, a communication 324 to a remote processing center 33 is automatically sent out. The remote processing center 33 is adapted to process the chemical measurements 311 in processing steps 331 independently of the local processing 313 using either more powerful processing routines of the type described above when referring to the local processing 313 or additional inputs to the processing compared to the input used during the local processing 313. The communication 324 therefore includes the raw data 312 or suitable data generated in processing steps which precede the calculation of the input 314.

The additional input can be drawn from sources 332 external to the portable device. These external sources can include other portable devices with the same or a similar type of integrated chemical sensor. The sources can include information collected from stationary sensors such as stations gathering pollution data or permanently installed chemical sensors. The sources 332 can include publically available data such as weather data, or information about chemical or other environmental accidents affecting the location of the portable device. When collecting the external information, the remote processing can include a system to activate an external sensor, for example by initiating a chemical measurement using a portable device in proximity to the portable device and comparing the results as gained from the two portable devices.

As output of the remote processing 331 at the remote facility 33, a new and likely improved result 333 is available. This re-calculated result can be applied in various ways. It can for example be re-tested for the first and second tests 321, 322 as described above or any equivalent tests. The re-testing can determine whether or not the input should have resulted in a negative outcome of the first test 321, in which case the portable device resumes its monitoring or measuring loop. Alternatively, the re-testing can determine whether or not the input gives a positive result at the second test 322, in which case the portable device raises a local alarm 323. As a matter of course, the remote facility is best enabled to raise alarms 334 in parallel to a transmission 335 of the re-calculated input 333 back to the portable device.

The diagram of FIG. 3B illustrates the effect of the re-calculations regarding the steps described above. It shows an initial locally calculated input 314 having passed the first test 321 but not the second test 322. As a result of the remote re-calculation the recalculated input 333 can be found either below the threshold set by the first test 321 or above the threshold set by the second test 322 as is indicated by the dashed arrows in FIG. 3B. In the case of such outcomes of the re-calculation the increased accuracy of the remote calculation increases the certainty of the alarm raising process by effectively narrowing the zone of uncertainty between the two tests 321, 322. It should be noted, however, an input 333 after re-calculation can remain within the zone of uncertainty between the two levels set by the respective tests 321, 322. Such an outcome would require another handling beyond the scope of this description.

While there are shown and described presently preferred embodiments of the invention, it is to be understood that the invention is not limited thereto but may be otherwise variously embodied and practised within the scope of the following claims. For example, it should be noted that the first and second test as described above can be replaced by a single test, a negative outcome of which sends the portable device into its measuring loop as described above, whereas a positive outcome initiates the transmission of the measurements to the remote processing facility for re-calculation. In such an example, an alarm would be raised only after a recalculation of the measurement.

The invention claimed is:

1. A chemical alert system for processing chemical sensor measurements, the system including
a portable electronic device,
a chemical sensor processing unit, and at least one chemical sensor integrated within a housing of the portable device and controlled by the chemical sensor processing unit, and wherein, the chemical sensor processing unit further comprises an alert discriminator configured for:

receiving an input based on measurements of the chemical sensor;

performing a test on the input; and based on an outcome of the test initiating a transfer of measurements of the chemical sensor to a remote processing facility for subsequent computerized processing of said measurements, wherein, said test comprises a first and a second test, the latter setting stricter conditions or thresholds than the first test, such that: based on an outcome of the first test an alert mode in the portable device is activated; and based on an outcome of the second test either a transfer of measurements is initiated or an alarm state of the portable device is activated, and wherein the alert discriminator is further configured such that passing of the second test causes the activation of the alarm state, whereas passing of the first test without passing of the second test initiates the transfer of measurements.

2. The system of claim 1, wherein the alert discriminator is configured for transferring measurements including:

measurements as used as input to the alert discriminator; and additional measurements as gained from any prior stage in a processing of the measurements including raw data representing direct sensor measurements of the at least one chemical sensor.

3. The system of claim 1, further configured such that an activation of the alarm state includes an activation of built-in elements of the portable device to generate an alarm.

4. The system of claim 1, further comprising the remote processing facility, the latter configured to:

receive the measurements of the chemical sensor as transferred by the portable device; and augment processing steps for the measurement of the chemical sensor as performed by the portable device.

5. The system of claim 4, wherein the remote processing facility is further configured such that augmented processing steps performed by the remote processing facility comprises an addition of further measurements or information from sources other than the portable device itself for use in the augmented processing steps.

6. The system of claim 1, wherein the chemical sensor comprises a metal-oxide sensing material.

7. The system of claim 1, wherein the chemical sensor is integrated onto a common substrate including CMOS circuitry.

8. The system of claim 1, wherein the portable electronic device is selected from a group comprising:

a mobile phone,
a handheld computer,
an electronic reader,
a tablet computer,
a game controller,
a pointing device,
a photo or a video camera,
a digital music player,
an electronic wrist watch,
a personal health tracking device,
a headset, and
a computer peripheral.

9. A method for processing chemical sensor measurements in a system including a portable electronic device and at least one chemical sensor integrated within a housing of the portable device and controlled by a chemical sensor processing unit, the latter comprising an alert discriminator, the method comprising, at the alert discriminator:

receiving an input based on measurements of the chemical sensor;

performing a test on the input; and based on an outcome of the test initiating a transfer of measurements of the chemical sensor to a remote processing facility for subsequent computerized processing of said measurement, wherein:

said test comprises a first and a second test, the latter setting stricter conditions or thresholds than the first test, such that: based on an outcome of the first test an alert mode in the portable device is activated; and based on an outcome of the second test either a transfer of measurements is initiated or an alarm state of the portable device is activated, and passing of the second test causes the activation of the alarm state, whereas passing of the first test without passing of the second test initiates the transfer of measurements.

10. A chemical alert system for processing chemical sensor measurements, the system including a portable electronic device, a chemical sensor processing unit, and at least one chemical sensor integrated within a housing of the portable device and controlled by the chemical sensor processing unit, and wherein, the chemical sensor processing unit further comprises an alert discriminator which is an electronic circuit or a processing unit programmed, designed, adapted or configured to execute the functions of receiving an input based on measurements of the chemical sensor;

performing a test on the input; and based on an outcome of the test initiating a transfer of measurements of the chemical sensor to a remote processing facility for subsequent computerized processing of said measurements, wherein said test comprises a first and a second test, the latter setting stricter conditions or thresholds than the first test, such that: based on an outcome of the first test an alert mode in the portable device is activated; and based on an outcome of the second test either a transfer of measurements is initiated or an alarm state of the portable device is activated, and wherein the alert discriminator is further configured such that passing of the second test causes the activation of the alarm state, whereas passing of the first test without passing of the second test initiates the transfer of measurements.

* * * * *